United States Patent [19]
Bildinov et al.

[11] Patent Number: 5,824,827
[45] Date of Patent: Oct. 20, 1998

[54] HALOGEN EXCHANGE REACTIONS

[75] Inventors: Igor Bildinov; Pavel Podsevalov; Tatjana Nazarenko; Leonid Deev, all of Perm, Russian Federation

[73] Assignee: Albemarle Corporation, Richmond, Va.

[21] Appl. No.: 754,338

[22] Filed: Nov. 22, 1996

[51] Int. Cl.⁶ .................................................. C07C 25/13
[52] U.S. Cl. .......................................................... 570/147
[58] Field of Search .............................................. 570/147

[56] References Cited

U.S. PATENT DOCUMENTS

| | | | |
|---|---|---|---|
| 3,064,058 | 11/1962 | Duesel et al. | 260/646 |
| 3,231,625 | 1/1966 | Nyman | 260/650 |
| 3,240,824 | 3/1966 | Boudakian et al. | 260/646 |
| 3,277,192 | 10/1966 | Fielding | 260/650 |
| 3,280,124 | 10/1966 | Boudakian et al. | 260/251 |
| 3,296,269 | 1/1967 | Boudakian | 260/290 |
| 3,300,537 | 1/1967 | Bennett et al. | 260/649 |
| 3,303,197 | 2/1967 | Haszeldine et al. | 260/290 |
| 3,312,746 | 4/1967 | Fielding | 260/650 |
| 3,314,955 | 4/1967 | Boudakian et al. | 260/251 |
| 3,334,150 | 8/1967 | Pierce et al. | 260/650 |
| 3,388,174 | 6/1968 | Fielding et al. | 260/650 |
| 3,408,412 | 10/1968 | Blackley et al. | 260/650 |
| 3,429,935 | 2/1969 | Wall et al. | 260/650 |
| 3,453,337 | 7/1969 | Bennett et al. | 260/650 |
| 3,485,839 | 12/1969 | Fuller | 260/251 |
| 3,574,775 | 4/1971 | Fuller | 260/650 |
| 3,852,365 | 12/1974 | Mahler | 260/650 F |
| 4,069,262 | 1/1978 | Kunz | 260/646 |
| 4,174,349 | 11/1979 | Evans et al. | 260/544 F |
| 4,209,457 | 6/1980 | Fuller | 260/465 G |
| 4,229,365 | 10/1980 | Oeser et al. | 260/465 G |
| 4,287,374 | 9/1981 | North | 568/937 |
| 4,684,734 | 8/1987 | Kaieda et al. | 546/345 |
| 4,937,397 | 6/1990 | Pews et al. . | |
| 4,978,769 | 12/1990 | Kysela et al. . | |

FOREIGN PATENT DOCUMENTS

| | | |
|---|---|---|
| 0003344 | 8/1979 | European Pat. Off. . |
| 678864 | 4/1994 | Russian Federation . |
| 755668 | 8/1956 | United Kingdom . |
| 866810 | 5/1961 | United Kingdom . |
| 970746 | 9/1964 | United Kingdom . |
| 996498 | 6/1965 | United Kingdom . |
| 1004375 | 9/1965 | United Kingdom . |
| 1026290 | 4/1966 | United Kingdom . |
| 1071323 | 6/1967 | United Kingdom . |
| 1256082 | 12/1971 | United Kingdom . |
| 1340421 | 12/1973 | United Kingdom . |

OTHER PUBLICATIONS

Finger et al., Aromatic Fluorine Compounds. VII. Replacement of Aromatic –Cl and NO₂ Groups by –F[1,2], JACS, 1956, vol. 78, pp. 6034–6037.

Fuller, Preparation of Polyfluoroaromatic Compounds by the Reaction of Perhalogeno–Aromatic Compounds with Potassium Fluoride in Sulpholan*, J. Chem. Soc., 1965, pp. 6264–6267.

Gottleib, The Replacement of Chlorine by Fluorine in Organic Compounds, JACS, 1936, 58, pp. 532–533.

Heller, Preparation of 3–Fluorophthalic Anhydride, J. Org. Chem., 1960, 25, pp. 834–835.

Holbrook et al., Fluorination of Perhalobenzenes with Potassium Fluoride in Polar Solvents, J. Org. Chem., 1966, 31, pp. 1259–1261.

Maynard, The Synthesis of Highly Fluorinated Compounds by Use of Potassium Fluoride in Polar Solvents, J. Org. Chem., 1963, vol. 28, pp. 112–115.

Starr et al., Dimethyl Sulphone as a Reaction Solvent for the Preparation of Aromatic Fluorides, Chemistry and Industry, 1962, pp. 1328–1329.

Aksenov et al., Interaction of Chloroaromatic Compounds with Alkali Metal Fluorides In The Presence of Crown–Ethers, Journal of Fluorine Chemistry, 28(1), 1985, pp. 73–87.

Birchall et al, Polyfluoroarenes. Part XVI. A Convenient Synthesis of Pentafluorobenzonitrile, J. Chem. Soc. (c), 1971, pp. 1341–1342.

Smyth et al., Inexpensive, Active KF for Nucleophillic Aromatic Displacement Reactions, Tetrahedron, vol. 51, No. 22, 1995, pp. 6363–6376.

Hitzke et al., No. 163—Preparation de derives perhalogenes aromatiques polyfluores par reaction d'echange d'halogene, utilisant une phase sel fondu, Bulletin De La Societe Chimique De France, 1974, No. 5–6, pp. 811–814.

Pearson et al., The Synthesis of Pentafluorobenzoic Acid and a New Purification of Chloropentafluorobenzene, Synthesis, p. 127, 1978 vol. 2.

Hitzke, La Fluoration de L'hexachlorobenzene et de la Pentachloropyridine en Milieu de Fluorure de Potassium Solide, Journal of Fluorine Chemistry, 16(2), 1980, pp. 103–128.

Kosolapoff, Aromatic Fluoro Derives. VIII. Reaction of Chloronitro Compounds with Fluorides of Alkali Metals, Chem Abstracts, vol. 57, 1962.

Banks et al., Heterocyclic Polyfluoro–Compounds. Part VI. Preparation of Pentafluoropyridine and Chorofluoropyridines from Pentachloroptridine, J. Chem. Soc., 1965, pp. 594–597.

Boudakian, Solvent–Free Fluorination of Partially–Chlorinated Heterocyclics: Synthesis of 2,6–Difluoropyridine from 2,6–Dichloropyridine, J. Heterocyclic Chem., 1968, vol. 5, pp. 683–684.

(List continued on next page.)

Primary Examiner—Alan Siegel
Attorney, Agent, or Firm—Philip M. Pippenger

[57] ABSTRACT

An essentially anhydrous agitated mixture of (i) finely-divided essentially anhydrous alkali metal fluoride (e.g., KF), (ii) haloaromatic compound having at least one halogen atom of atomic number greater than 9 on an aromatic ring (e.g., $C_6Cl_6$), and (iii) an aminophosphonium catalyst (e.g., $(Et_2N)_4PBr$), is heated at a temperature at which fluorine replaces one or more of the ring halogen atom of the haloaromatic compound.

30 Claims, 1 Drawing Sheet

OTHER PUBLICATIONS

Bunnett et al., Chemical Reviews—Vol. 48, Aromatic Nucleophilic Substitution Reactions, pp. 273, 277, 405, 1951.

Chambers et al., Polyfluoro–Heterocyclic Compounds. Part I. The Preparation of Fluoro–, Chlorofluoro–, and Chlorofluorohydro–Pyridines., J. Chem. Soc., 1964, pp. 3573–3576.

Finger et al., Aromatic Fluorine Compounds. XI. Replacement of Chlorine by Fluorine in Halopyridines., J. Org. Chem., 1963, 28, pp. 1666–1668.

Finger et al., Aromatic Fluorine Compounds. VIII. Plant Growth Regulators and Intermediates, JACS, 1959, 81, pp. 94–101.

FIGURE 1

HALOGEN EXCHANGE REACTIONS

TECHNICAL FIELD

This invention relates to halogen exchange reactions involving haloaromatic compounds and alkali metal fluorides, and more particularly to improved processes for producing polyfluorinated aromatics by catalyzed halogen exchange reactions.

BACKGROUND

Halogen exchange reactions for fluorinating haloaromatic compounds using alkali metal fluorides have been extensively studied heretofore. Typically they involve the reaction of a chloroaromatic compound with potassium fluoride, rubidium fluoride or cesium fluoride by heating the reactants to extremely high temperatures (above about 400° C.) in the absence of an ancillary diluent or solvent, or by conducting the reaction at temperatures of around 200°–230°0 C. in an aprotic solvent such as sulfolane. It has also been reported that organic fluorine compounds such as pentafluorobenzonitrile, tetrafluorophthalonitriles and pentafluoropyridine can be formed by reacting a corresponding chloro- or bromo-substituted compound with alkali metal halide such as potassium fluoride in benzonitrile as solvent at 190° C. to 400° C. in a sealed autoclave under autogenous pressure.

Use of catalysts in some exchange reactions has also been studied. Such catalysts have included quaternary ammonium salts, metal carbonyls, crown ethers and cryptates.

In most cases, the halogen exchange reaction is sluggish and tends to form product mixtures in which yields of polyfluorinated aromatics are relatively low, especially if the haloaromatic compound used is a polyhaloaromatic compound free from activating functionality such as nitro or carbonyl. For example, with hexachlorobenzene and potassium fluoride, typical product mixtures contain a mixture of co-products including hexafluorobenzene together with various chlorofluorobenzenes.

A need presently exists for a commercially feasible process whereby the halogen exchange reaction as applied to a wide variety of haloaromatic compounds may be conducted in large scale reaction equipment under relatively mild reaction conditions while providing commercially acceptable yields of the desired products. In addition, a particularly welcome contribution to the art would be the provision of a process whereby fluorinated perhaloaromatic compounds such as chloropentafluorobenzene and hexafluorobenzene can be produced on a large scale in good yield under relatively mild reaction conditions.

This invention is deemed to fulfill these needs most expeditiously.

SUMMARY OF THE INVENTION

This invention provides a new catalytic halogen exchange reaction using an alkali metal fluoride as the fluorine source. The process enables production of a wide variety of fluorinated aromatic compounds under relatively mild reaction conditions. Moreover, the process is applicable to use as starting materials of haloaromatic compounds containing one or more halogen atoms other than fluorine, including compounds which are devoid of activating groups, as well as compounds which possess one or more activating groups in the molecule. In fact, the process is especially well adapted for polyfluorination of perhaloaromatic compounds such as hexachlorobenzene, hexabromobenzene, pentachlorofluorobenzene, tetrachlorodifluorobenzene, trichlorotrifluorobenzene, dichlorotetrafluorobenzene, etc., which have no activating group in the molecule. In addition, the catalyzed process can be conducted with smaller excesses of the alkali metal fluoride than generally required in prior processes.

The substantial improvements made possible by this invention are brought about at least in part by use of an aminophosphonium catalyst in the process. As an example of such improvements, comparative studies on a 50-liter scale have shown that in reactions using hexachlorobenzene and potassium fluoride to form chloropentafluorobenzene and hexafluorobenzene, the inclusion of the aminophosphonium catalyst, tetrakis(diethylamino)phosphonium bromide, pursuant to this invention resulted in the following yield improvements:

a) Yields of desired products based on raw material inputs were increased from 12% to 25%.

b) Yields of desired products based on hexachlorobenzene input were increased from 35% to 95%.

c) Molar yields of desired products were increased from 49% to 86%.

Thus, in accordance with this invention there is provided in one of its embodiments a halogen exchange process which comprises heating an essentially anhydrous agitated mixture formed from ingredients comprising (i) at least one finely-divided essentially anhydrous alkali metal fluoride, (ii) at least one haloaromatic compound having on an aromatic ring at least one halogen atom of atomic number greater than 9, and (iii) an aminophosphonium catalyst, at one or more reaction temperatures at which at least one said halogen atom of said haloaromatic compound is replaced by a fluorine atom.

In a preferred embodiment of this invention, the process is conducted using as the initial haloaromatic compound(s) for the halogen exchange, at least one haloaromatic compound that is devoid of any activating functional group on the aromatic ring to which the halogen atom of atomic number greater than 9 is bonded.

A particularly preferred embodiment involves using as the initial haloaromatic ingredient to be subjected to the halogen exchange processing, one or more haloaromatic compounds that are not only devoid of any activating functional group on the aromatic ring to which the halogen atom of atomic number greater than 9 is bonded, but in addition have no hydrogen atom on that aromatic ring. Especially preferred haloaromatic compounds of this type are perhaloaromatic compounds of the formula $C_6Cl_nBr_mF_p$ where n is from 0 to 6, m is from 0 to 6 and p is from 0 to 5, and where the sum of n, m and p is 6. Compounds in which m is zero have been used with outstanding success.

Another preferred embodiment includes conducting the process of this invention such that the essentially anhydrous agitated mixture when heated to one or more reaction temperatures is predominately a mixture of solids dispersed in a continuous liquid phase. Operations wherein the continuous liquid phase comprises at least one halogen-free, polar, anhydrous aprotic solvent constitute additional preferred embodiments of this invention.

Preferred catalyst ingredients for use in the various process embodiments of this invention are tetra(dihydrocarbylamino)phosphonium halides.

These and other embodiments, features and advantages of this invention will be further apparent from the ensuing description, accompanying drawing, and appended claims.

FURTHER DESCRIPTION OF THE INVENTION

The basic feed materials to the process of this invention are one or more haloaromatic compounds containing one or more ar-halogen atoms other than fluorine, alkali metal fluoride(s) of one or more alkali metals other than lithium (preferably alkali metal of atomic number 19 or above), and one or more aminophosphonium catalysts. Use of one or more ancillary solvents or diluents is optional, but preferable.

Haloaromatic Ingredient

Any aromatic compound that has at least one replaceable halogen atom other than fluorine on the aromatic ring is a candidate ingredient for use in the process. The compound may have a homocyclic aromatic nucleus (i.e., at least one benzene ring system) or a heteroaromatic ring system. Also, the compound may contain one or more activating groups such as nitro, nitroso, carbonyl, cyano, sulfonic acid, etc., or it may be devoid of any such group. The compound contains one or more chlorine, bromine or iodine atoms, or any combination of Cl, Br, and/or I atoms on the aromatic ring and may also have one or more such halogen atoms on one or more side chains and/or on one or more non-aromatic homocyclic or heterocyclic rings bonded or fused to the aromatic ring system. In addition the compound may contain one or more fluorine atoms anywhere in the molecule including one or more ar-fluorine atoms provided the compound has at least one aromatic ring that contains at least one replaceable ar-halogen atom other than fluorine. The hetero atom in the halo-substituted aromatic ring where the fluorine substitution is desired is from 1 to 3 nitrogen atoms (e.g., the compound is, or has at least the ring system of, an ar-halopyridine, an ar-halopyridazine, an ar-halopyrimidine, an ar-halopyrazine, an ar-halotriazine where at least one ar-halogen atom is other than a fluorine atom). Other hetero atoms which can be present in side chains or additional ring systems of the compound include one or more nitrogen, oxygen, sulfur, phosphorus, boron or silicon atoms, or combinations of two or more of these. Generally speaking, the haloaromatic ingredient may contain in the range of up to 50 carbon atoms in the molecule, and preferably contains in the range of up to 20 carbon atoms in the molecule.

Preferred are haloaromatic compounds that are devoid of any activating group(s) in the molecule, as these usually undergo a halogen exchange reaction much less readily than their counterparts which have activating functionality in the molecule.

As between the homocyclic and heterocyclic haloaromatics, the homocyclic haloaromatics are preferred ingredients. As noted above, haloaromatics that are devoid of any activating functional group on the aromatic ring to which the halogen atom of atomic number greater than 9 is bonded and in addition, are devoid of any hydrogen atom on that aromatic ring constitute another preferred category of haloaromatic ingredient or feed material for the process. Especially preferred haloaromatic compounds of this type are perhaloaromatic compounds of the formula $C_6Cl_nBr_mF_p$ where n is from 0 to 6, m is from 0 to 6 and p is from 0 to 5, and where the sum of n, m and p is 6. Compounds in which m is zero are especially desirable ingredients because of good reactivity in the process and generally lower cost. Moreover, there is a particularly pressing present need for methods for effectively producing polyfluorobenzenes, especially chloropentafluorobenzene and hexafluorobenzene, from their polychloro analogs such as hexachlorobenzene, pentachlorofluorobenzene, tetrachlorodifluorobenzene, trichlorotrifluorobenzene, or dichlorotetrafluorobenzene, or mixtures of any two or more of these, a need fulfilled by this invention.

Also fulfilled by this invention is the need for a method for effectively producing bromopentafluorobenzene from its polybromo analogs such as hexabromobenzene, pentabromofluorobenzene, tetrabromodifluorobenzene, tribromotrifluorobenzene, or dibromotetrafluorobenzene, or mixtures of any two or more of these.

Other haloaromatic compounds which can be converted into ar-fluorinated compounds by use of this invention include, for example, mono-, di-, tri-, tetra- and pentachlorobenzenes, and bromo and iodo analogs thereof; mono and polychloro, bromo and iodo naphthalenes, tetrahydronaphthalenes, acenaphthalenes, biphenyls and terphenyls; alkyl- and haloalkyl-substituted analogs of the foregoing; chloro, bromo and iodo diarylethers and monoalkylmonoaryl ethers; 2-chloronitrobenzene; 4-chloronitrobenzene; 2,4-dinitrochlorobenzene; 3,4-dichloronitrobenzene; 3-chloro-4-fluoronitrobenzene; 2,4,6-trichloropyrimidine; tetrachloropyrimidine; 2-chlorobenzonitrile; 4-chlorobenzonitrile; pentachlorobenzonitrile; tetrachloroisophthalonitrile; 2-chloropyridine; 2,5-dichloropyridine; pentachloropyridine; 4-chlorophthalic anhydride; and still other similar compounds, such as are referred to in U.S. Pat. No. 4,684,734 to Kaieda, et al.

Alkali Metal Fluoride Ingredient

Potassium fluoride, rubidium fluoride, and cesium fluoride are the preferred alkali metal halides used in the practice of this invention because of their higher reactivity in the exchange reaction. However, sodium fluoride can be used, especially where the haloaromatic ingredient has activating functionality on the haloaromatic ring, and in cases where only partial replacement of ar-chloride, ar-bromide or ar-iodide is desired.

Combinations of any two or more of the alkali metal fluorides can be used, including combinations in which lithium fluoride is present. Thus, mixtures of potassium fluoride, rubidium fluoride and/or cesium fluoride together with sodium fluoride or lithium fluoride, or both, can also be used if desired, although this is not recommended. To enhance its reactivity, the alkali metal fluoride should be in finely-divided or powdery anhydrous form. Potassium fluoride is the preferred fluorinating agent as it is the most cost effective reagent. One convenient way of ensuring that the fluorinating agent is suitably anhydrous is to form a slurry of the fluoride salt in a suitable volatile hydrocarbon such as benzene that forms an azeotrope with water, and heat the mixture to dryness, while of course suitably handling and disposing of the vapors. A particularly useful form of potassium fluoride for use in the process is the active form of KF produced using the procedure described by T. P. Smyth, A. Carey and B. K. Hodnett in *Tetrahedron,* Volume 51, No. 22, pp. 6363–6376 (1995). In brief, the procedure involves recrystallizing KF from a methanol solution by slow evaporation of the solvent, followed by drying at 100° C. Another useful form of potassium fluoride is KF dispersed on $CaF_2$. This material is described by J. H. Clark, A. J. Hyde and D. K. Smith in *J. Chem. Soc. Chem. Commun,* 1986, 791. Other activated forms of KF such as spray dried KF (N. Ishikawa, et al. *Chem. Letts,* 1981, 761), and freeze dried KF (Y. Kimura, et al. *Tetrahedron Letters,* 1989, 1271) can be used. It is also deemed possible to apply one or more of the foregoing activating procedures to other alkali metal fluorides such as cesium fluoride and/or sodium fluoride. The entire disclosure of each of the four papers cited in this paragraph is incorporated herein by reference.

The proportions of alkali metal fluoride to the haloaromatic ingredient(s) being used can be varied. In theory there is no upper limit on the amount of alkali metal fluoride used relative to the amount of haloaromatic compound(s) used. If a very large excess of alkali metal fluoride is used relative to the amount of replaceable halogen present in the haloaromatic ingredient(s) present, the latter becomes the limiting reactant and the excess alkali metal halide remains as such. When the reaction is performed in the absence of an ancillary diluent, an excess amount of the alkali metal fluoride can serve to facilitate stirring or other agitation of the reaction mixture, and thus to this extent use of a suitable excess of alkali metal fluoride can be beneficial. Nevertheless, beyond a certain level of excess alkali metal fluoride, common sense and practicality come into play. Thus ordinarily the amount of alkali metal fluoride will not exceed about 10 or 15 mols per mol of replaceable halogen in the initial haloaromatic ingredient(s) used, and in most cases will be less than this. If on the other hand the amount of replaceable halogen in the haloaromatic ingredient(s) used exceeds the molar quantity of alkali metal fluoride used, the latter becomes the limiting reactant. Thus in most cases this factor will also be taken into consideration when selecting the proportions for use in any given reaction. Generally speaking, the reactants will often be employed in proportions falling in the range of from about 0.8 to about 5 mols of alkali metal fluoride per mol of replaceable halogen in the haloaromatic ingredient(s) used therewith, and in some preferred cases such as where an ancillary diluent is employed, the reactants will be charged in proportions in the range of from about 1 to about 3 mols of alkali metal fluoride per mol of replaceable halogen in the haloaromatic ingredient(s) used therewith.

Aminophosphonium Catalyst Ingredient

An essential catalyst ingredient of this invention is at least one aminophosphonium catalyst ingredient. One or more other co-catalysts may also be included, if desired, as long as at least one aminophosphonium catalyst ingredient is charged, concurrently or in any sequence, into the reaction zone or reaction mixture. Use of the aminophosphonium catalyst without use of a co-catalyst is currently deemed preferable.

The aminophosphonium catalysts are preferably charged in the form of tetra(dihydrocarbylamino)phosphonium halides. Such compounds can be represented by the formula:

where each R is, independently, a hydrocarbyl group, preferably an alkyl group, and X is a halogen atom, preferably a fluorine or bromine atoms, and most preferably a bromine atom. Examples of such aminophosphonium compounds are:

tetrakis(diethylamino)phosphonium fluoride
tetrakis(dibutylamino)phosphonium bromide
tris(diethylamino)(dipropylamino)phosphonium iodide
tetrakis(dibutylamino)phosphonium iodide
tris(dibutylamino)(diethylamino)phosphonium iodide
tris(dipropylamino)(diheptylamino)phosphonium iodide
tetrakis(dipropylamino)phosphonium bromide
tris(diethylamino)(dihexylamino)phosphonium iodide
tris(diethylamino)(dibutylamino)phosphonium iodide
tris(dipropylamino)(heptylpropylamino)phosphonium iodide
tetrakis(dipropylamino)phosphonium iodide
tris(dipropylamino)(ethylpropylamino)phosphonium iodide
tetrakis(diethylamino)phosphonium iodide
tetrakis(diethylamino)phosphonium bromide
tetrakis(diphenylamino)phosphonium bromide
tetrakis(di-m-tolylamino)phosphonium bromide
tetrakis(dibenzylamino)phosphonium bromide
tetrakis(dicyclohexylamino)phosphonium bromide
tetrakis(dioctylamino)phosphonium bromide
tetrakis(didecylamino)phosphonium bromide
tetrakis(diethylamino)phosphonium chloride.

One preferred group of aminophosphonium catalyst in the form as charged to the reactor is comprised of the tetra (dialkylamino)phosphonium chlorides and/or bromides. Of these, the aminophosphonium catalyst ingredient is more preferably one or more tetra(dialkylamino)phosphonium bromides in which the alkyl groups can be the same or different and each has up to about 12 carbon atoms. At present, the most preferred compound is tetrakis (diethylamino)phosphonium bromide. For a method for the preparation of such compounds, see Koidan, Marchenko, Kudryavtsev, and Pinchuk, *Zh. Obshch. Khim.*, 1982, 52, 2001, an English language translation of which is available from Plenum Publishing Corporation.

The aminophosphonium catalyst is used in catalytically effective amounts, and such amounts typically fall in the range of about 3 to about 6 mol %, and preferably in the range of about 4 to about 5 mol %, based on the total amount (in mols) of the haloaromatic compound(s) with which the aminophosphonium catalyst is being associated in the reaction zone.

Co-catalyst Ingredient

The tetra(dihydrocarbylamino)phosphonium halide catalysts are effective when utilized as the only catalyst component charged directly or indirectly (i.e., after admixture with one or more other components being charged to the reaction system). Such catalytic mode of operation is preferred. However, as noted above, one or more co-catalyst ingredients may be used, if desired.

One type of such co-catalyst materials is comprised of one or more crown ethers or crypt compounds. These compounds, sometimes referred to as "cage compounds" can prove helpful in further enhancing the reactivity of the alkali metal fluoride. See in this connection, U.S. Pat. No. 4,174,349 to Evans, et al. A full description of the crown ethers and the crypt compounds is provided in the Evans, et al. patent and references cited therein relating to these materials, namely U.S. Pat. No. 3,687,978; J. J., Christensen, et al., *Chem. Rev.*, 1974, 74, 351; J. S. Bradshaw, et al., *Heterocycl. Chem.*, 1974, 11, 649; C. J. Pedersen, et al., *Angew. Chem. Int. Ed. Engl.*, 1972, 11, 16; the Technical Bulletin of PCR Incorporated entitled KRYPTOFIX; and *J. Org. Chem*, 1977, Vol 42, No. 10, 2A. The crown ether or crypt compound is used in a catalytically effective amount, which typically is in the range of 0.01 to 1 mol per mol of haloaromatic compound(s) in the reaction mixture.

Another type of co-catalyst that can be used is composed of (i) at least one polyvalent inorganic fluoride of boron, aluminum, tin, phosphorus, titanium, zirconium, hafnium, or silicon, or (ii) at least one double salt of the polyvalent inorganic fluoride and alkali metal fluoride, or (iii) a combination of (i) and (ii), with the proviso that the inorganic fluoride of (i), (ii) and (iii) is in a stable valency state so that (i), (ii) and (iii), as the case may be, has no oxidizing properties. U.S. Pat. No. 3,453,337 to Bennett, et al., reports that in the uncatalyzed reaction between hexachlorobenzene and KF or NaF, the inclusion of compounds of the types (i), (ii) and (iii) above provides enhanced product yields using milder reaction conditions and shorter reaction times. Examples of suitable polyvalent compounds include $LiBF_4$, $NaBF_4$, $KBF_4$, $K_2SnF_6$, $KPF_6$, $K_2SiF_6$, $Na_2TiF_6$, $K_2TiF_6$, $Na_2ZrF_6$, $K_2ZrF_6$, $Na_2HfF_6$, $K_2HfF_6$, among others. Such compounds can be used in catalytically effective amounts of up to 50% or more of the weight of the alkali metal fluoride charged to the reaction mixture. Typically the amount will fall in the range of about 2 to about 25% of the weight of alkali metal fluoride used.

Other co-catalysts which may be considered for use include quaternary ammonium salts such as described for example by J. Dockx, *Synthesis* 1973, 441; C. M. Starks and C. Liotta, Phase Transfer Catalysts, 1978, Academic Press, New York; and W. P. Weber and G. W. Gokel, *Phase Transfer Catalysis in Organic Synthesis* 1977, Springer-Verlag, Berlin-Heidelberg-New York); and metal carbonyls such as described by M. F. Semmelhack and H. T. Hall, *J. Am. Chem. Soc.*, 1974, 96, 7091.

The aminophosphonium catalyst and the above co-catalyst(s), if used, can vary both in function and in composition. As to function, they can serve to promote or enhance the fluorination exchange reaction, e.g., (a) by increasing reaction rate without affecting yield or selectivity, (b) by increasing yield or selectivity, or both, without affecting reaction rate, or (c) by increasing reaction rate and improving yield or selectivity, or both. Thus the term "catalyst" or "co-catalyst" is used herein to denote that the material in the manner used improves or enhances the reaction process in some way or other so that the inclusion or presence of that material or its progeny in the reaction mixture provides at least one beneficial consequence of its use. The mechanism by which it exerts its effect(s) is of no consequence, provided of course that the advantage(s) of its use outweigh(s) the disadvantage(s), if any, of its use.

As regards catalyst and co-catalyst composition, the material is identified herein as to its composition prior to being combined with any other substance being used in the process. After addition to, and/or mixing with, one or more other ingredients used in the process and/or during the course of the process itself, the catalyst may change in its composition, and if so, the resultant changed material, whatever its makeup and however many changes it may undergo, may be responsible in whole or in part for the functioning of the catalyst.

Process Conditions

The process can be conducted by dry mixing the finely-divided essentially anhydrous alkali metal fluoride, the haloaromatic compound having at least one halogen atom of atomic number greater than 9 on an aromatic ring, and an aminophosphonium catalyst, and heating the mixture at one or more reaction temperatures at which at least one such halogen atom of the haloaromatic compound is replaced by a fluorine atom. Alternatively, the foregoing ingredients may be heated to one or more such reaction temperatures while in admixture with an ancillary solvent/diluent. The solvent or diluent used is preferably a polar aprotic solvent such as, for example, sulfolane (tetramethylene sulfone), N,N-dimethylformamide, N,N-dimethylacetamide, dimethylsulfone, dimethylsulfoxide, triglyme (triethylene glycol dimethyl ether), N-methyl pyrrolidinone, or benzonitrile, or mixtures of two or more of such materials. Other solvent/diluents for use in the process are haloaromatics that are in the liquid state at least at, and preferably below, the reaction temperature(s) being employed. Examples include hexafluorobenzene, octafluorotoluene, perfluorodecalin, dichlorotetrafluorobenzene, trichlorotrifluorobenzene and tetrachlorodifluorobenzene. The last three such compounds are especially desirable as solvent/diluents when producing pentachlorofluorobenzene as they not only serve as solvent/diluents, but as reactants as well.

Whether the reaction mixture is formed with or without a solvent/diluent, the reaction mixture should be thoroughly agitated during the course of the reaction to ensure intimate contact among the different materials in the mixture. Thus use of mechanical agitation equipment such as mechanical stirrers, rocking autoclaves, or similar apparatus is highly recommended.

Reaction temperatures will typically be in the range of about 150° C. to about 350° C. and preferably in the range of about 170° C. to about 250° C., and more preferably in the range of about 170° C. to about 220° C. The reaction may be conducted at atmospheric, sub-atmospheric or super-atmospheric pressures. In many cases it is desirable as well as convenient to carry out the reaction in a closed system at autogenous pressures. Alternatively, the reaction may be carried out in a liquid phase under reflux conditions. Reaction periods will typically fall in the range of about 2 to about 48 hours, and preferably in the range of about 5 to about 20 hours. It will be appreciated that on the basis of this disclosure, departures from any of the ranges of proportions and/or reaction conditions given above may be made whenever such departures are deemed necessary or desirable.

The following examples are for the purpose of illustration and not limitation.

EXAMPLES 1–12

Figure 1:
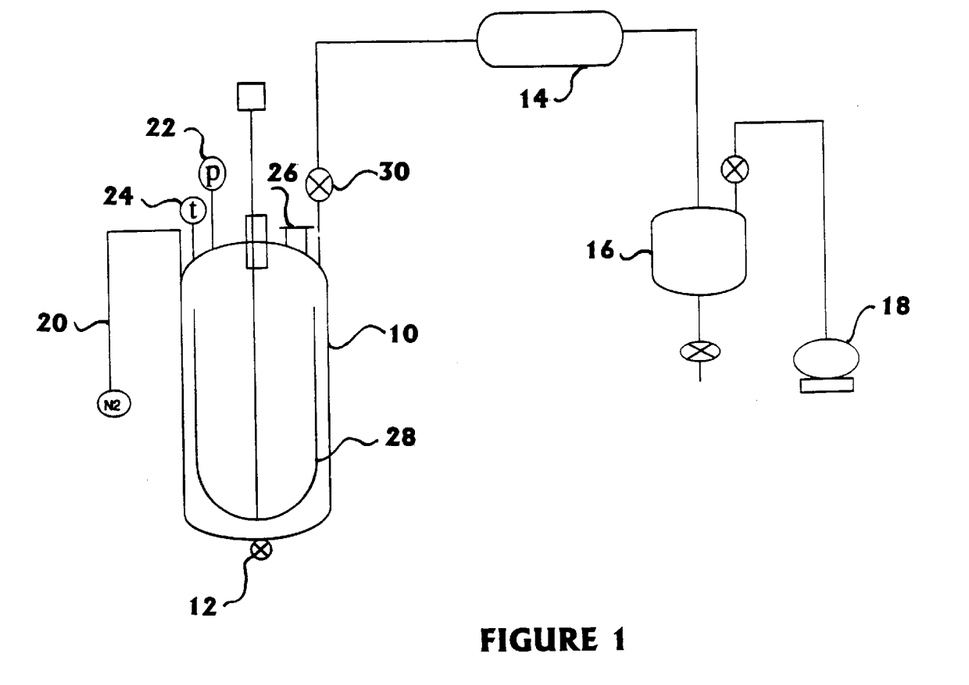
FIG. 1 illustrates schematically a batch type plant facility for conducting the process without use of an ancillary solvent/diluent.

A facility of the type schematically depicted in FIG. 1 is used. It comprises a 50-liter capacity stainless steel reactor (316S) 10 fitted with an electrical heating system (not depicted), bottom discharge valve 12, vapor condenser 14, receiver 16, vacuum system 18, a pressure release system (not depicted) that operates via the overheads, nitrogen line 20 for vacuum breaking, pressure gauge/monitor 22, temperature gauge/monitor 24, and manway 26 for solids charging. Reactor 10 is capable of operating at working pressures up to 125 psi, and vacuum system 18 has the capability of operating to 10 mmHg pressure. Agitator 28 is preferably a modified gate-type agitator having scraping knife-edges on the gate agitator to minimize sticking of the semi-molten paste-like reaction mass especially at the reactor wall. The facility should also include a spray drier (not depicted).

In the operation of the facility freshly prepared anhydrous potassium fluoride is used for each batch. This is conveniently prepared by forming a 40% weight/volume solution of potassium fluoride, heating the solution to the boiling point and pumping the solution via a dried atomizer into a drier operated at 350°–400° C., e.g., 370° C. The dry powder is placed into suitable containers and used immediately. Alternatively, an activated form of KF such as referred to above, or a commercially available spray dried KF (whether milled or not milled), can be used. Before initiating a reaction, steps should be taken to ensure that the reactor 10 and the overheads are clean and dry, that all systems are operational, and that all raw materials are available for use. In addition the system should be checked to ensure that the bottom valve 12 is closed. If there is any doubt as regards vessel dryness, the reactor should be heated to 105° C. with full vacuum applied for two hours. After two hours the vessel should be allowed to cool while under vacuum. At ambient temperature the vacuum is then broken with nitrogen, and at this point the reaction procedure may be commenced.

At the start of the batch operation, reactor agitator 28 should be activated to be sure that the agitator is running smoothly. To the reactor with the agitator in operation, 21 kg of dry potassium fluoride powder is charged via manway 26. Then through the manway are charged 15 kg of hexachlorobenzene followed by 0.96 kg of tetrakis(diethylamino) phosphonium bromide. Manway 26 and valve 30 are closed. The reactor contents are then heated over a period of one hour to 180° C. It is important to use this rapid heating to ensure sufficient agitation of this particular reaction mixture. During the heating the pressure in the reactor rises gradually. When the reactor contents reach 180° C., the reactor heating controls are adjusted to provide a heating rate increase of 4° C. per six hours. The reactor contents are allowed to heat up over this rate over 42 hours, (7 increments of temperature increase for a total temperature increase of 28° C.). Slow heating at this stage of the process is important to ensure adequate mixing of this particular reaction mixture. At this point the reaction mixture should have reached a temperature of approximately 208° C. and the internal pressure of the reactor is monitored hourly. When the pressure does not vary between two successive hourly readings, the reaction can be deemed to have proceeded to completion. When the pressure becomes constant in the range of 75–100 psi the heating system is turned off and the reactor is allowed to cool. At this point valve 30 is cautiously opened to allow the pressure to vent from the reactor to condenser 14 and thence to receiver 16. When ambient pressure is reached in the reactor nitrogen is slowly introduced via nitrogen line 20. Vacuum system 18 is put into operation to provide a vacuum of about 725 mmHg to reactor 10. The nitrogen bleed to the reactor is slowly reduced while observing the rate of distillate recovery to receiver 16 to ensure that distillate recovery is not excessive. The vacuum is then gradually increased while continuing to monitor distillate recovery rate until maximum (flat) vacuum is achieved. When the system reaches ambient temperature the vacuum is broken with nitrogen, the vacuum system is shut off, and then the nitrogen bleed is discontinued. The reaction product mixture is then recovered from the reactor through valve 12. The reactor is cleaned with boiling aqueous caustic solution, washed with water and dried. A series of 12 batch operations was conducted generally in accordance with this procedure. The facility was as described except that in Examples 1 and 2, a low speed gate agitator was used. Because of tackiness of the reaction mixture, portions of the mixture tended to stick to the reactor wall. This problem was reduced by changing the agitator used in the remainder of the operations so that it included the above-referred-to knife-blades on the gate agitator. The conditions and results of these 12 runs are summarized in the Table along with the conditions and results of a control run where no catalyst was used. The acronyms in the Table are: HCB is hexachlorobenzene, CPFB is chloropentafluorobenzene, and DCTFB is dichlorotetrafluorobenzene.

dichlorotetrafluorobenzene flash distilled from the respective reaction mixtures. Fractional distillation of the combined products from Examples 1–12 matched these analytical results almost exactly. Examples 1–12 yielded 104.765 kilograms of mixed chlorofluorobenzenes. The bulk fractional distillation resulted in the isolation and recovery of:

41.085 kg of Hexafluorobenzene
43.020 kg of Chloropentafluorobenzene
11.440 kg of Dichlorotetrafluorobenzene Each such product assayed 99% minimum purity.

It is to be noted that in the above examples, the catalyzed process of this invention was conducted at a maximum temperature of 208° C. without use of any added ancillary solvent or diluent. A conventional non-catalyzed non-solvent reaction of hexachlorobenzene with potassium fluoride typically involves use of 20-liter autoclaves operating at a temperature of 450° C. and a pressure of up to 1,500 psi and employs an 85% excess of potassium fluoride. Based on total raw material input, batch yield of desired products, is around 12%.

As indicated above, one highly preferred form of alkali metal fluoride is an activated KF formed by recrystallizing KF from methanol solution by slow evaporation of the solvent at reduced pressure followed by drying at an elevated temperature. The following is an illustrative laboratory procedure that may be used for conducting this operation, which procedure is based on that described by T. P. Smyth, A. Carey and B. K. Hodnett in *Tetrahedron*, Volume 51, No. 22, pp. 6363–6376 (1995). KF is dissolved in excess dry methanol (e.g., in proportions of about 1 part by weight of KF per about 13 to about 20 parts by weight of methanol). This operation is preferably conducted under a dry nitrogen atmosphere, and preferably the methanol used is 99.9+% A.C.S. HPLC grade packaged under nitrogen. The methanol is slowly removed at reduced pressure at a temperature in the range of about 25° to about 35° C. (e.g., 30° C.) and then dried in vacuo at one or more temperatures in the range of about 70° to about 120° C. (e.g., 100° C.) for a period of at least about 5 hours (e.g. 6 hours). Preferably the activated KF is used promptly after it has been prepared.

A number of modifications in the process are possible without departing from the scope of this invention. By way of illustration and not limitation, the following modifications are presented:

a) The catalyst or catalyst residues may be recycled.

TABLE

| Ex. No. | KF Charged, kg | HCB Charged, kg | Catalyst Charged, kg | Molar Ratio, KF:HCB | Reaction Time, hr | HFB Yield, kg | CPFB Yield, kg | DCTFB Yield, kg | Conversion of HCB, % | % Molar Yield HFB + CPFB |
|---|---|---|---|---|---|---|---|---|---|---|
| Control | 34.0 | 15.0 | None | 11.1:1 | 24 | 2.5 | 2.5 | — | — | 49 |
| 1 | 15.4 | 11.0 | 0.97 | 6.866:1 | 60 | 2.555 | 2.608 | 0.7353 | 77.64 | 69 |
| 2 | 15.4 | 11.0 | 0.98 | 6.866:1 | 82 | 2.4336 | 2.8137 | 0.6253 | 77.67 | 70 |
| 3 | 15.4 | 11.0 | 0.98 | 6.866:1 | 32 | 3.0964 | 2.9500 | 0.7906 | 90.21 | 81 |
| 4 | 21.0 | 15.0 | 1.30 | 6.867:1 | 22.5 | 3.7200 | 4.0000 | 1.2090 | 85.98 | 76 |
| 5 | 21.0 | 15.0 | 1.03 | 6.867:1 | 20 | 3.7011 | 4.2515 | 0.1900 | 78.95 | 78 |
| 6 | 21.0 | 15.0 | 1.03 | 6.867:1 | 46 | 4.5472 | 2.8490 | 1.8282 | 88.96 | 73 |
| 7 | 21.0 | 15.0 | 0.942 | 6.867:1 | 38 | 3.9763 | 4.1376 | 0.1900 | 81.09 | 79 |
| 8 | 21.0 | 15.0 | 0.96 | 6.867:1 | 44 | 3.9861 | 3.8378 | 0.7416 | 83.16 | 77 |
| 9 | 21.0 | 15.0 | 0.96 | 6.867:1 | 29.5 | 2.7824 | 4.1454 | 1.9082 | 83.86 | 67 |
| 10 | 21.0 | 15.0 | 0.96 | 6.867:1 | 34.5 | 3.1420 | 4.1447 | 1.7954 | 86.54 | 71 |
| 11 | 21.0 | 15.0 | 0.96 | 6.867:1 | 46 | 4.3521 | 4.1302 | 1.2931 | 94.41 | 83 |
| 12 | 21.0 | 15.0 | 0.96 | 6.867:1 | 46 | 4.4160 | 4.3008 | 1.1232 | 95.19 | 86 |

In the Table, reaction time is the time from reaching reaction temperature of 190° C. and yields of products are expressed as kilograms derived from analysis of the fraction of hexafluorobenzene, chloropentafluorobenzene and b) When the desired product is a polyfluoroaromatic compound, intermediates formed that contain a lesser than desired number of fluorine atoms per molecule may be recycled.

c) If the desired product has suitably high volatility, it may be removed from the reaction zone during the course of the reaction, e.g., essentially as soon as it is formed, so as to prevent or at least minimize overfluorination.

d) Special procedures, e.g., drying by azeotropic distillation or by high temperature spray drying, may be employed for drying the alkali metal fluoride before use.

e) Multistage drying procedures may be used for drying the alkali metal fluoride before use.

f) The alkali metal fluoride may be micronized or reduced to a colloidal state in one or more stages prior to use.

g) Combinations of one or more drying stages with one or more micronizing stages, or vice versa, may be applied to the alkali metal fluoride before use.

h) Whether operating with or without an ancillary solvent, the alkali metal fluoride may be an optimized mixture composed of a major amount of dry, finely-divided potassium fluoride with a minor reaction-enhancing amount of dry, finely-divided cesium fluoride.

i) When producing a desired product having one or more intermediates that are in the liquid state at or below the selected reaction temperature(s), such intermediates may be employed as solvent/diluents in the process.

j) The proportions of the selected ingredients for use in any given situation may, and should be, optimized by performing carefully designed pilot experiments and scale-up trials before settling upon the mode of operation in a large scale commercial facility.

k) In lieu of or in addition to one or more simple alkali metal fluorides, e.g. KF, the alkali metal reactant may be or include a more complex alkali metal salt such as a double salt, examples of which include $KBF_4$, $CsBF_4$, $NaBF_4$, $K_3AlF_6$, $K_2SnF_6$, $Cs_2SnF_6$, $KPF_6$, $CsPF_6$, $K_2SiF_6$, $Cs_2SiF_6$, $Na_2TiF_6$, $K_2TiF_6$, $Na_2ZrF_6$, $K_2ZrF_6$, $Na_2HfF_6$, $K_2HfF_6$, among others.

l) In lieu of or in addition to one or more aminophosphonium catalysts of the type described herein, corresponding aminoarsonium compounds, $[(R_2N)_4As]X$, or aminoantimonium compounds, $[(R_2N)_4Sb]X$, where where R and X are as defined above, may be used as catalyst or co-catalyst ingredients.

m) Simple quaternary phosphonium salts such as tetraethylphosphonium bromide, tetraphenylphosphonium bromide, tetraethylphosphonium chloride, tetraphenylphosphonium chloride, tetraethylphosphonium iodide, tetraphenylphosphonium iodide, etc., may be used as co-catalyst ingredients.

An example of one such modification which constitutes an embodiment of this invention relates to the synthesis of chloropentafluorobenzene and/or hexafluorobenzene from hexachlorobenzene. In this process the alkali metal fluoride ingredient used preferably comprises potassium fluoride, and the aminophosphonium catalyst ingredient used is preferably at least one tetra(dialkylamino)phosphonium halide (especially tetra(diethylamino)phosphonium bromide), and the agitated mixture formed from hexachlorobenzene, potassium fluoride, and the aminophosphonium catalyst ingredient is heated at one or more reaction temperatures in the range of 170° to 220° C. for at least a substantial portion of the reaction. In this particular embodiment the agitated mixture comprises solids suspended or dispersed in continuous liquid phase, which preferably comprises a major amount (preferably 60 volume % or more at the outset of the reaction) of at least one chloro-fluoro-perhalobenzene that is in the liquid state at least while the agitated mixture is at one or more reaction temperatures in the range of 170° to 220° C. Examples of such chloro-fluoro-perhalobenzenes include dichlorotetrafluorobenzene (b.p. at atmospheric pressure, approximately 151° C.), trichlorotrifluorobenzene (m.p., approximately 62° C.), and tetrachlordifluorobenzene (m.p., approximately 138° C.). Of these, dichlorotetrafluorobenzene is particularly desirable as it is a liquid at room temperature and can readily be kept in the liquid state at temperatures in the range of 170° to 220° C. by conducting the reaction at suitable superatmospheric pressures.

It is to be understood that the ingredients referred to by chemical name or formula anywhere in the specification or claims hereof, whether referred to in the singular or plural, are identified as they exist prior to coming into contact with another substance referred to by chemical name or chemical type (e.g., another reactant, a solvent, a diluent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and other materials are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance or ingredient as it existed at the time just before it was first contacted, blended or mixed with one or more other substances or ingredients in accordance with the present disclosure. The fact that the substance or ingredient may have lost its original identity through a chemical reaction or transformation or complex formation or assumption of some other chemical form during the course of such contacting, blending or mixing operations, is thus wholly immaterial for an accurate understanding and appreciation of this disclosure and the claims thereof. Nor does reference to an ingredient by chemical name or formula exclude the possibility that during the desired reaction itself an ingredient becomes transformed to one or more transitory intermediates that actually enter into or otherwise participate in the reaction. In short, no representation is made or is to be inferred that the named ingredients must participate in the reaction while in their original chemical composition, structure or form.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A halogen exchange process which comprises heating an essentially anhydrous agitated mixture formed from ingredients comprising (i) at least one finely-divided essentially anhydrous alkali metal fluoride, (ii) at least one haloaromatic compound having at least one halogen atom of atomic number greater than 9 on an aromatic ring, and (iii) an aminophosphonium catalyst, at one or more reaction temperatures at which at least one said halogen atom of said haloaromatic compound is replaced by a fluorine atom.

2. A process according to claim 1 wherein the aminophosphonium catalyst ingredient comprises at least one tetra(dihydrocarbylamino)phosphonium halide.

3. A process according to claim 1 wherein the aminophosphonium catalyst ingredient is at least one tetra (dialkylamino)phosphonium chloride and/or bromide.

4. A process according to claim 1 wherein the aminophosphonium catalyst ingredient is one or more tetra (dialkylamino)phosphonium bromides in which the alkyl groups can be the same or different and each has up to about 12 carbon atoms.

5. A process according to claim 1 wherein the aminophosphonium catalyst ingredient is tetrakis(diethylamino) phosphonium bromide.

6. A process according to any of claims 1–5 inclusive taken individually wherein the alkali metal atoms of said alkali metal fluoride ingredient have an atomic number of 19 or more.

7. A process according to any of claims 1–5 inclusive taken individually wherein said alkali metal fluoride ingredient is principally or exclusively potassium fluoride.

8. A process according to any of claims 1–5 inclusive taken individually wherein ingredient (ii) is at least one haloaromatic compound ingredient devoid of any activating functional group on the aromatic ring to which said halogen atom of atomic number greater than 9 is bonded.

9. A process according to any of claims 1–5 inclusive taken individually wherein said haloaromatic compound ingredient is at least one perhaloaromatic compound of the formula $C_6Cl_nBr_mF_p$ where n is from 0 to 6, m is from 0 to 6 and p is from 0 to 5, and where the sum of n, m and p is 6.

10. A process according to any of claims 1–5 inclusive taken individually wherein said haloaromatic compound ingredient is at least one perhaloaromatic compound of the formula $C_6Cl_nF_p$ where n is from 1 to 6, and p is from 0 to 5, and where the sum of n and p is 6.

11. A process according to claim 1 wherein said perhaloaromatic compound ingredient includes at least hexachlorobenzene, dichlorotetrafluorobenzene or trichlorotrifluorobenzene, or any combination of any two or all three of the foregoing.

12. A process according to claim 2 wherein said perhaloaromatic compound ingredient is hexachlorobenzene.

13. A process according to any of claims 1–5 taken individually wherein a vapor phase mixture of perhalobenzenes is formed from which at least one of the more volatile perhalobenzene components is separated and recovered from one or more less volatile perhalobenzene components of said vapor phase mixture; and wherein at least a portion of said one or more less volatile perhalobenzene components is recycled to the present or a subsequent halogen exchange reaction.

14. A process according to any of claims 1–5 inclusive taken individually wherein said essentially anhydrous agitated mixture at least prior to heating is predominately a solid phase mixture.

15. A process according to any of claims 1–5 inclusive taken individually wherein said essentially anhydrous agitated mixture at least when heated to at least one of said one or more reaction temperatures is predominately a mixture of solids dispersed in a continuous liquid phase comprising at least one halogen-free, polar, anhydrous, aprotic solvent.

16. A process according to claim 3 wherein said essentially anhydrous agitated mixture at least when heated to at least one of said one or more reaction temperatures is predominately a mixture of solids dispersed in a continuous liquid phase comprising at least one halogen-free, polar, anhydrous aprotic solvent; and wherein said essentially anhydrous agitated mixture is heated at one or more reaction temperatures in the range of 150° to 350° C. for at least a substantial portion of the reaction.

17. A process according to claim 1 wherein the alkali metal fluoride ingredient comprises potassium fluoride, wherein the perhaloaromatic compound ingredient comprises hexachlorobenzene, wherein the aminophosphonium catalyst ingredient is at least one tetra(dialkylamino) phosphonium halide, and wherein the agitated mixture is heated at one or more reaction temperatures in the range of 170° to 220° C. for at least a substantial portion of the reaction.

18. A process according to claim 17 wherein said agitated mixture comprises solids suspended or dispersed in continuous liquid phase.

19. A process according to claim 18 wherein said continuous liquid phase comprises a major amount of at least one chloro-fluoro-perhalobenzene that is in the liquid state at least while the agitated mixture is at one or more reaction temperatures in the range of 170° to 220° C.

20. A process according to claim 1 wherein said finely-divided essentially anhydrous alkali metal fluoride is an activated form of alkali metal fluoride in which the alkali metal atoms have an atomic number of 19 or more.

21. A process according to claim 1 wherein said finely-divided essentially anhydrous alkali metal fluoride comprises an activated form of potassium fluoride.

22. A process according to claim 1 wherein said finely-divided essentially anhydrous alkali metal fluoride is an activated form of potassium fluoride formed by recrystallizing KF from methanol solution by slow evaporation of the solvent at reduced pressure followed by drying at an elevated temperature.

23. A process according to claim 1 wherein said finely-divided essentially anhydrous alkali metal fluoride comprises an activated form of potassium fluoride; wherein the aminophosphonium catalyst ingredient is at least one tetra (dialkylamino)phosphonium chloride and/or bromide; wherein a vapor phase mixture of perhalobenzenes comprising chloropentafluorobenzene and at least dichlorotetrafluorobenzene or trichlorotrifluorobenzene, or both, is formed; wherein chloropentafluorobenzene is separated and recovered from one or more less volatile perhalobenzene components of said vapor phase mixture; and wherein at least a portion of said one or more less volatile perhalobenzene components is recycled to the present or a subsequent halogen exchange reaction.

24. A process according to claim 23 wherein said essentially anhydrous agitated mixture at least prior to heating is predominately a solid phase mixture.

25. A process according to claim 23 wherein said essentially anhydrous agitated mixture at least when heated to at least one of said one or more reaction temperatures is predominately a mixture of solids dispersed in a continuous liquid phase comprising at least one halogen-free, polar, anhydrous aprotic solvent.

26. A halogen exchange process which comprises:
a) forming a mixture from ingredients comprising (i) at least one finely-divided alkali metal fluoride in which the alkali metal atoms have an atomic number of 19 or more, (ii) at least one haloaromatic compound having at least one halogen atom of atomic number greater than 9 on an aromatic ring which is devoid of any activating functional group in the molecule, and (iii) an aminophosphonium catalyst;

b) heating the mixture with agitation at one or more reaction temperatures at which and for a period of time during which at least one said halogen atom of said haloaromatic compound is replaced by a fluorine atom; and c) recovering at least one haloaromatic compound in which at least one said halogen atom thereof has been replaced by a fluorine atom.

27. A process according to claim 26 wherein said mixture at least prior to the heating of b) is predominately a solid phase mixture.

28. A process according to claim 27 wherein said alkali metal fluoride consists essentially of potassium fluoride; wherein said at least one haloaromatic compound consists essentially of at least one perhaloaromatic compound of the formula $C_6Cl_nF_p$ where n is from 1 to 6, and p is from 0 to 5, and where the sum of n and p is 6; and wherein said catalyst consists essentially of at least one tetra (dialkylamino)phosphonium bromide.

29. A process according to claim 26 wherein the ingredients used in forming said mixture further include at least one halogen-free, polar, aprotic solvent in an amount sufficient to form a continuous liquid phase such that on agitation, a mixture of solids dispersed in said liquid phase is formed.

30. A process according to claim 29 wherein said alkali metal fluoride consists essentially of potassium fluoride; wherein said at least one haloaromatic compound consists essentially of at least one perhaloaromatic compound of the formula $C_6Cl_nF_p$ where n is from 1 to 6, and p is from 0 to 5, and where the sum of n and p is 6; and wherein said catalyst consists essentially of at least one tetra (dialkylamino)phosphonium bromide.

* * * * *